United States Patent
Han et al.

(10) Patent No.: US 9,606,052 B2
(45) Date of Patent: Mar. 28, 2017

(54) TUNING-FORK BASED NEAR FIELD PROBE FOR SPECTRAL MEASUREMENT, NEAR-FIELD MICROSCOPE USING THE SAME, AND SPECTRAL ANALYSIS METHOD USING NEAR-FIELD MICROSCOPE

(71) Applicant: POSTECH ACADEMY-INDUSTRY FOUNDATION, Pohang-si, Gyeongsangbuk-do (KR)

(72) Inventors: Hae Wook Han, Pohang-si (KR); Young Woong Do, Daegu-si (KR); Ki Won Moon, Pohang-si (KR)

(73) Assignee: POSTECH ACADEMY-INDUSTRY FOUNDATION, Pohang-si, Gyeongsangbuk-Do (KR)

( * ) Notice: Subject to any disclaimer, the term of this patent is extended or adjusted under 35 U.S.C. 154(b) by 0 days.

(21) Appl. No.: 14/339,955

(22) Filed: Jul. 24, 2014

(65) Prior Publication Data
US 2015/0028210 A1 Jan. 29, 2015

(30) Foreign Application Priority Data
Jul. 29, 2013 (KR) ........................ 10-2013-0089529

(51) Int. Cl.
*G01N 21/35* (2014.01)
*G01N 21/3586* (2014.01)
(Continued)

(52) U.S. Cl.
CPC ......... *G01N 21/35* (2013.01); *G01N 21/3586* (2013.01); *G01Q 30/02* (2013.01); *G01Q 60/22* (2013.01)

(58) Field of Classification Search
CPC ............... G01N 21/35; G01N 21/3568; G01N 21/3563; Y10S 977/862
See application file for complete search history.

(56) References Cited

U.S. PATENT DOCUMENTS 5,212,987 A * 5/1993 Dransfeld .............. B82Y 20/00
73/105
5,742,377 A 4/1998 Minne et al.
(Continued)

FOREIGN PATENT DOCUMENTS

JP 2001-4519 1/2001
JP 2002-148172 5/2002
(Continued)

OTHER PUBLICATIONS

A. Naber, et al., "Dynamic force distance control suited to various probes for scanning near-field optical microscopy", p. 3955-3961; Review of Scientific Instruments, 1999. vol. 70, No. 10, Oct. 1999; American Institute of Physics.

Primary Examiner — Yara B Green
(74) Attorney, Agent, or Firm — Kile Park Reed & Houtteman PLLC

(57) ABSTRACT

The present invention is provided to remove scattering from other parts, except for an end part of a nano-probe, in a near-field microscope, and to enable a spectral analysis by delaying the generation of multiple reflections caused through the shaft of the nano-probe. A first characteristic of the present invention is to temporally delay generation of multiple reflections by manufacturing a probe portion to have a predetermined length or more in a tuning-fork based near-field probe. A second characteristic of the present invention is to provide a near-field microscope which includes a tuning-fork based near-field probe having a structure as above, and can measure a time-domain transient reaction of a scattered wave. A third characteristic of the present invention is to provide a method for performing a spectral analysis on a time-domain signal measured by the near-field microscope.

21 Claims, 17 Drawing Sheets

(51) Int. Cl.
    *G01Q 30/02*     (2010.01)
    *G01Q 60/22*     (2010.01)

(56) References Cited

U.S. PATENT DOCUMENTS

| | | | | |
|---|---|---|---|---|
| 6,046,448 | A * | 4/2000 | Sato | B82Y 20/00 |
| | | | | 250/225 |
| 6,094,971 | A * | 8/2000 | Edwards | B82Y 35/00 |
| | | | | 73/105 |
| 6,194,711 | B1 * | 2/2001 | Tomita | B82Y 20/00 |
| | | | | 250/216 |
| 6,240,771 | B1 * | 6/2001 | Giessibl | B82Y 35/00 |
| | | | | 250/307 |
| 6,396,050 | B1 * | 5/2002 | Yamamoto | B82Y 20/00 |
| | | | | 250/216 |
| 6,525,808 | B1 * | 2/2003 | Jackson | G01N 21/41 |
| | | | | 250/234 |
| 6,710,331 | B2 | 3/2004 | Narita et al. | |
| 7,511,512 | B2 | 3/2009 | Sekiguchi | |
| 2004/0159781 | A1 * | 8/2004 | Akiyama | B82Y 35/00 |
| | | | | 250/234 |
| 2006/0152232 | A1 * | 7/2006 | Shvets | G01R 31/2822 |
| | | | | 324/750.02 |
| 2007/0113630 | A1 * | 5/2007 | Matsumoto | B82Y 35/00 |
| | | | | 73/105 |
| 2008/0054168 | A1 * | 3/2008 | Hoshino | B82Y 20/00 |
| | | | | 250/216 |

FOREIGN PATENT DOCUMENTS

| | | |
|---|---|---|
| JP | 2004-533604 | 11/2004 |
| JP | 2010-271297 | 12/2010 |
| JP | 2012-52848 | 3/2012 |
| KR | 10-2013-0032088 | 4/2013 |

* cited by examiner

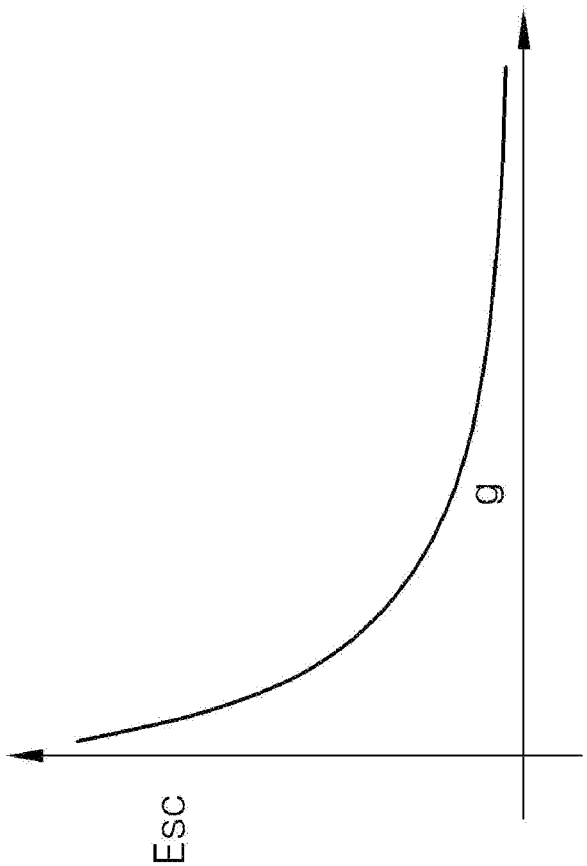
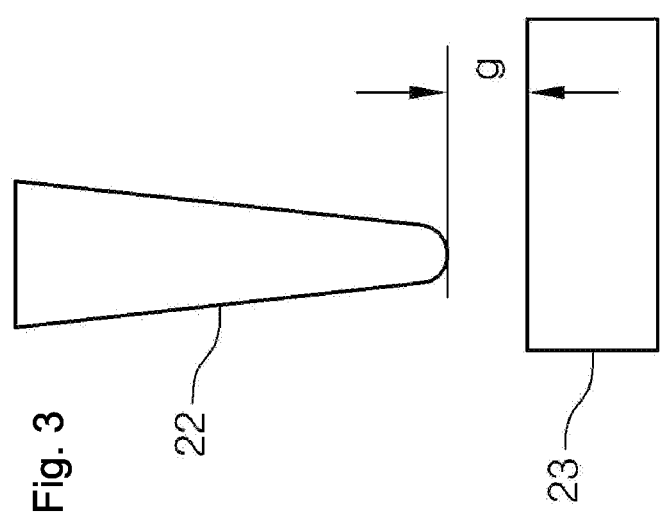
Fig. 3

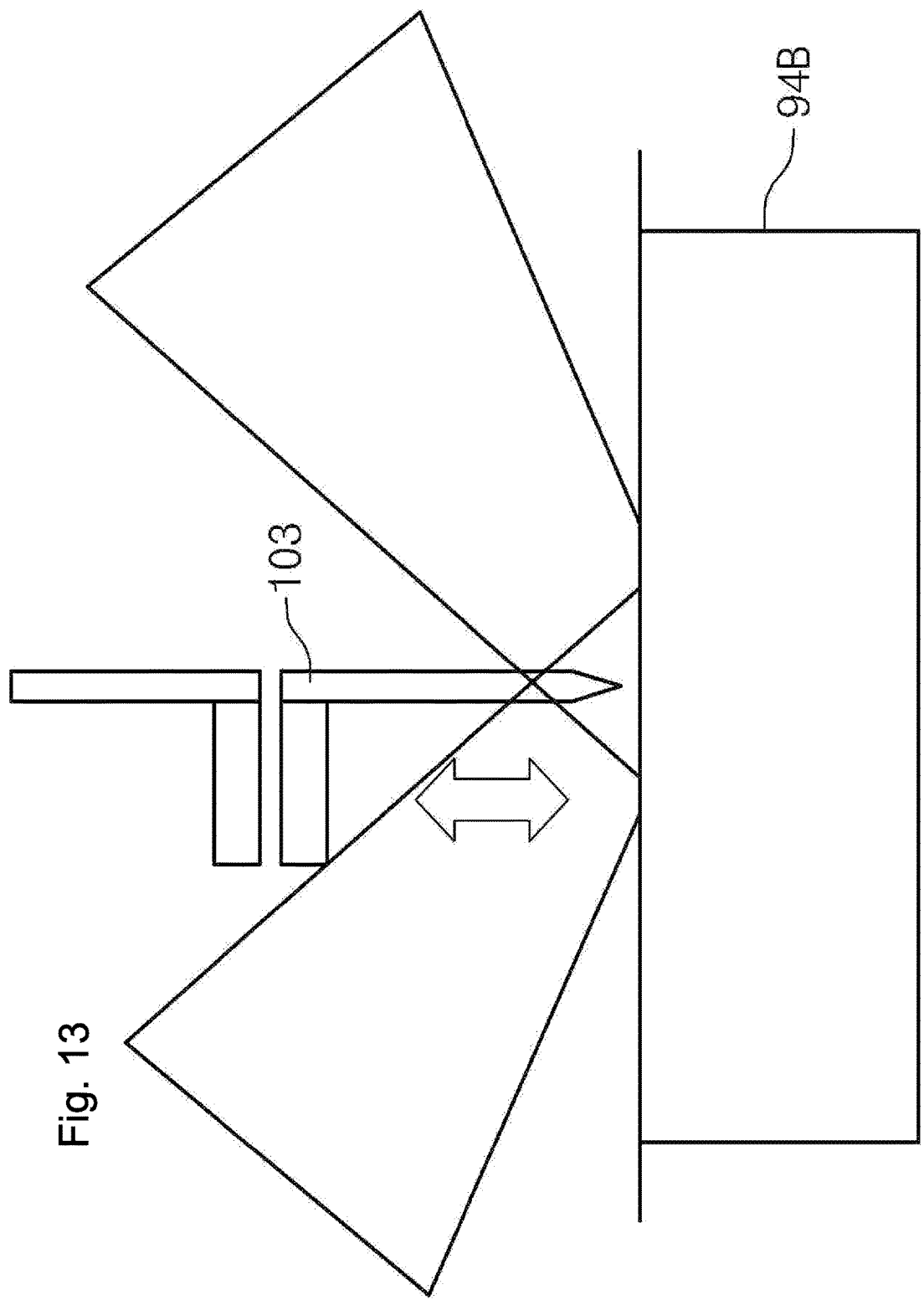

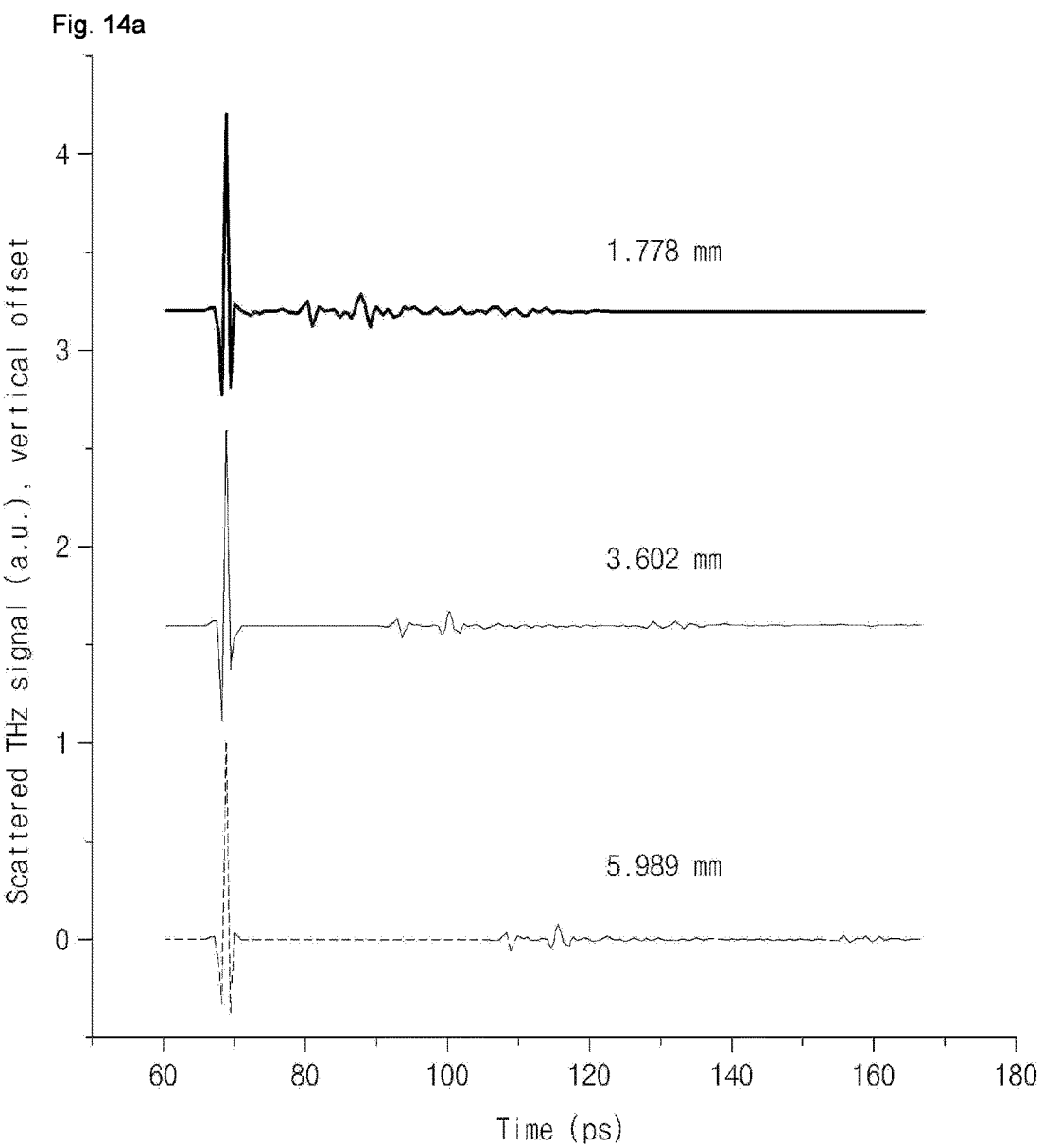

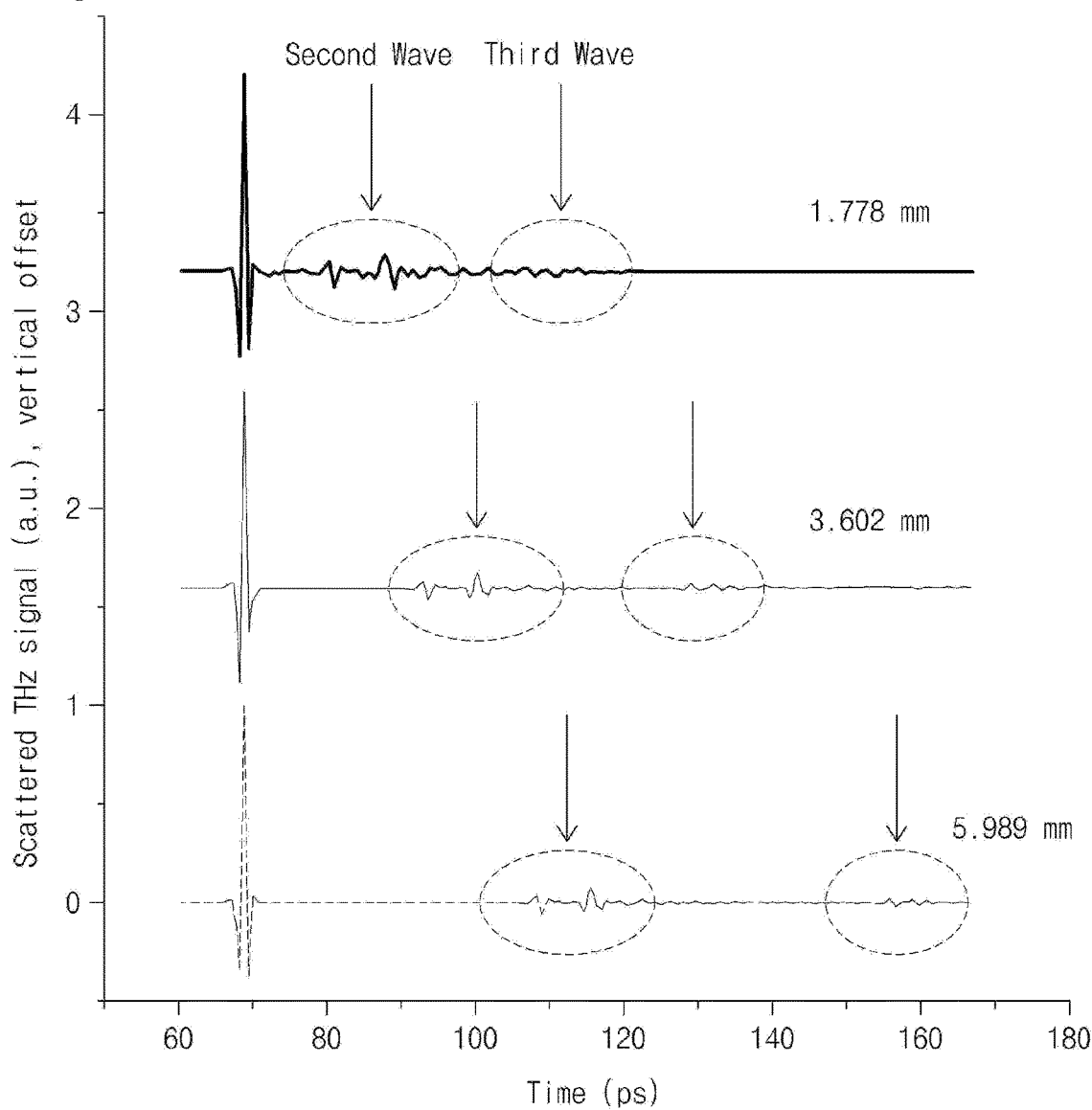

TUNING-FORK BASED NEAR FIELD PROBE FOR SPECTRAL MEASUREMENT, NEAR-FIELD MICROSCOPE USING THE SAME, AND SPECTRAL ANALYSIS METHOD USING NEAR-FIELD MICROSCOPE

BACKGROUND OF THE INVENTION

Technical Field

The present invention relates to a near-field probe for a broadband spectral measurement with a nanometer-level resolution, and more particularly, to a tuning-fork based near-field probe which enables a spectral measurement by preventing multiple reflections by the antenna effect of a probe unit from appearing and by reducing the amount of generation of background scattering signals at portions, except for the tip of a nano-probe; a near-field microscope using the near-field probe; and a spectral analysis method using the near-field microscope.

Background Art

An optical microscope is used to view the structures of a living body or a nano-device in units of nanometers, or the shape of the surface thereof. Such an optical microscope allows an object to be viewed with light, so that there is a limit in resolving power due to the limit of diffraction. Generally, the resolving power of an optical microscope is limited to about a half of the wavelength of light used in the microscope.

With the appearance of a near-field microscope (NFM), the limit of diffraction is overcome, so that it becomes possible to obtain an optical image with a resolution less than the wavelength of light. A near-field microscope is a device which is configured: to have a structure in which force microscope technology using a probe, as an atomic force microscope (AFM), and optical measurement technology are combined; and to read, through the tip of a probe, a near field existing within a distance less than the wavelength of light from the surface of a material to be inspected. Differently from an electric field or a magnetic field propagating in a free space, a near field, which is restrained on the boundary surface between materials, can exist in the distribution of a size less than the wavelength. Since such a near field does not propagate into a free space, it is impossible to view from an exterior, but it is possible to read restrained light through a nano-sized probe.

There are various types of near-field microscopes, wherein a near-field microscope can be implemented by utilizing the probe of an atomic force microscope (AFM) as a probe for a near field. An AFM enables acquisition of the topography of a sample with a nano-level high resolution; combining an optical method therewith enables the distribution of an optical constant (e.g. a permittivity, a magnetic permeability, or the like) of a material to obtained with a high resolving power which is almost the same level as the resolution of the AFM; and, through this, what is the material can be identified.

At present, the highest resolving power is achieved by an apertureless type near-field microscope. This technology is implemented in such a manner as to incident light on the nano-probe unit of an AFM or a force microscope similar to the AFM, and to remotely measure a scattered wave generated from the tip of the probe unit. Depending on the wavelength of used light, a wavelength at which an optical constant is to be measured is determined. When a broadband variable-wavelength light source is used, an optical constant spectrum can be obtained in a wide wavelength band, thereby implementing broadband spectroscopy with a nanometer-level resolution.

Meanwhile, a terahertz frequency band corresponds to electromagnetic waves having the frequencies of 0.1 to tens of THz, and is located between an optical wave and an electronic wave. At present, research and development for light sources, detectors, and application technology in connection with the frequency are being actively conducted.

As spectral technology in the terahertz frequency band, a terahertz time-domain spectroscopy (THz-TDS) using a pulse light source is widely used. A pulse light source may be regarded as a broadband light source the phase of which accords in view of a frequency band. When a broadband pulse in a terahertz band passes through a specific material, the spectral characteristic of the material is reflected in the pulse, thereby causing a change in the pulse. By analyzing the change, a broadband terahertz spectral measurement on a sample is completed.

FIG. 1 is a block diagram illustrating a conventional terahertz time-domain spectroscope to which the terahertz time-domain spectroscopy is applied. As shown in FIG. 1, the conventional terahertz time-domain spectroscope includes an ultrafast pulse laser 10, a plurality of beam splitters 11, a mechanical chopper 12, a mechanical optical delay line 13, an InAs wafer 14, a sample 15, a terahertz detector (THz detector) 16, a lock-in amplifier 17, and a control personal computer (control PC) 18.

Referring to FIG. 1, the fast-pulse laser 10 generates a terahertz pulse. The terahertz pulse is generated by the InAs wafer (THz emitter) 14 through the plurality of beam splitters 11, the mechanical chopper 12, and the mechanical optical delay line 13. Accordingly, a terahertz pulse having a bandwidth of about 0-2.5 THz with duration of 0-1 ps is generated from the InAs wafer 14. In order to generate a terahertz wave, an electro-optic crystal (EO-crystal), a photoconductive antenna (PC antenna), or the like may be used, instead of the InAs wafer 14.

The terahertz pulse generated as above penetrates the sample 15 on a moving stage through a parabolic mirror or the like. Then, the terahertz pulse which has penetrated the sample 15 is inputted to an electrode unit of the terahertz detector 16. At the moment when the terahertz pulse is inputted to the terahertz detector 16 through the route, the terahertz detector 16 comes to have conductivity, wherein the duration of the conductivity is much shorter than the duration of the terahertz pulse.

In the terahertz detector 16, current flows by an electric field generated by the input terahertz pulse (i.e. probe pulse), in which the amount of current is proportional to the intensity of the electric field. For the terahertz detection, an electro-optic crystal (EO crystal) may be used instead of the photo-conductive antenna.

Since the time interval between the terahertz pulse generated by the InAs wafer through the photoexcitation by the femtosecond laser 10 and the probe pulse inputted to the terahertz detector 16 can be adjusted through the mechanical optical delay line 13, the terahertz detector 16 can measure the intensity of the electric field in a time domain.

The intensity of the electric field measured by the terahertz detector 16 is inputted to the control PC 18 through the lock-in amplifier 17, and a measured time-domain signal is Fourier-transformed by the control PC 18 and is analyzed in a frequency domain. Accordingly, the broadband sample characteristic of the sample 15 can be measured.

An optical image of the sample 15 can be obtained by raster-scanning the sample through the moving stage. In this case, the resolution is determined by the size of the focus of a terahertz wave focused on the sample 15, and is limited to a half of wavelength.

In order to overcome such limitation in resolution, various attempts have been made. Representatively, a concept of a terahertz scattering-type scanning near field optical microscope (THz s-SNOM) capable of measuring a near filed in a terahertz band by combining a terahertz time-domain spectral system using a broadband pulse light source with a non-aperture type near-field microscope system, as shown in FIG. 1, has been proposed and researched.

In the THz s-SNOM, a sample is attached on a piezo-stage, and a nano-probe is mounted above the sample and vibrates in a perpendicular direction with respect to the sample. A cantilever-type near-field probe widely used in a commercial AFM has been generally used as the nano-probe.

FIG. 2 illustrates conventional technology of using a cantilever-type near-field probe, wherein, as illustrated therein, a structure in which a probe 22 is connected to a one-side end of a cantilever 21 in a direction perpendicular to the cantilever 21 is provided.

A PID control is performed on the piezo-stage, and thus the average distance between the sample and the tip 22-1 of the probe is constantly maintained. In such a state, the topography of the sample can be obtained by scanning the sample.

The THz detector measures the mixed signal of a wave reflected from the surface of the sample, and a scattered wave from the nano-probe. Generally, since the scattered wave at the tip 22-1 of the nano-probe 20 is extremely weak as compared with an incident wave, it may be difficult to extract a scattered wave at the tip 22-1 of the nano-probe 20 from a measured signal. The non-linear characteristic of the scattered wave is used to measure the scattered wave.

FIG. 3 illustrates the non-linear characteristic of the scattered wave. As shown in FIG. 3, the scattered wave at the tip 22-1 of the nano-probe 20 has a characteristic that the scattered wave non-linearly increases as the distance "g" between the tip 22-1 of the probe and the sample 23 is decreased. This results from a near-field interaction between the tip 22-1 of the probe and the sample 23.

Therefore, as illustrated in FIG. 4, the scattered wave at the tip 22-1 of the probe can be detected by obtaining a difference between a waveform detected by the terahertz detector when the tip 22-1 of the probe is close to the sample 23, and a waveform detected by the terahertz detector when the tip 22-1 of the probe is relatively far away from the sample 23. The scattered wave shows a characteristic that is extremely susceptible to the distance between the tip 22-1 of the probe and the sample 23. In contrast, other components of terahertz wave which is detected by the detector, such as reflected waves and the like, are not largely influenced by the distance between the tip 22-1 of the probe and the sample 23. Therefore, with a difference as described with respect to FIG. 4, a scattered wave component from the tip 22-1 of the probe can be extracted. In practice, a scattered wave modulated by a vibrating nano-probe is demodulated using a lock-in amplifier, so that a measurement is achieved.

FIG. 5 illustrates various scattering sources which exist in a conventional THz s-SNOM system. When the vibration frequency of a probe is set as "$\Omega$", a signal modulated by the probe may be expressed as Equation 1 below.

$$E(t) = \sum_n E_b^n \cos\Omega t + \sum_n E_{Tip}^n \cos\Omega t \quad (1)$$

As expressed in FIG. 5 and by Equation 1, a scattered wave Eb generated from the body or base part of a cantilever-type nano-probe 20 is modulated by an angular velocity "$\Omega$", together with a scattered wave generated from the tip 22-1 of the nano-probe 20. Thus, when a signal is demodulated through the lock-in amplifier, the scattered wave Eb is reflected in a demodulated signal generated through the lock-in amplifier although the scattered wave Eb is not the scattered wave generated from the tip 22-1 of the nano-probe 20. This is called "background scattering". In order to remove such background scattering and to extract a scattering signal, a harmonic of "$2\Omega$" or "$3\Omega$" has been used instead of "$\Omega$".

In a THz s-SNOM system including a broadband pulse light source and an electric field detector, when a terahertz time-domain scattered wave is measured, the body part 22 of a probe functions as a wave guide. Accordingly, a phenomenon that an incident wave is propagated to the base part 22-2 of the probe along the body 22 of the probe appears.

Then, the wave arriving at the base part is reflected to generate second and third scattering signals. The scattering signals generated as above complicate the analysis of a frequency domain, thereby disabling a spectral analysis through a Fourier transform of a measured signal.

FIG. 6 is a view illustrating a wave guide effect and a multiple reflection phenomenon of the base part of a probe in a conventional cantilever-type nano-probe.

FIG. 8 is a view illustrating a scattered wave generation area in a conventional cantilever-type nano-probe. Referring to FIG. 8, in a long wavelength range such as a terahertz band, the beam radius of a focus of a terahertz beam focused on a nano-probe on a sample by a parabolic mirror is larger than the structure of a cantilever-type nano-probe due to the limit of diffraction. For this reason, it is inevitable to generate background scattering, and thus many difficulties are caused in measuring the optical characteristic of an object to be measured.

In addition, since scattering signals are periodically generated due to the multiple reflections and the wave guide effect of the cantilever-type nano-probe, the broadband information of a sample is mixed with the periodically scattering signals, and thus there is a difficulty in a quantitative broadband analysis. Referring to "(a)" of FIG. 7, multiple pulses appear close to each other in a time domain due to multiple reflections caused on the base part of a nano-probe, as shown in FIG. 6, and a transient response of a first pulse is mixed with second and third pulses, thereby making it impossible to separate the transient response by the first pulse. In addition, as shown in "(b)" of FIG. 7, although a Fourier transform is performed for a frequency analysis, it is impossible to analyze the broadband characteristic of the sample due to the antenna effect of the nano-probe.

DISCLOSURE

Technical Problem

Accordingly, the present invention has been made in an effort to solve the problems occurring in the related art, and a first object of the present invention is to provide a tuning-fork based near-field probe which has a structure capable of reducing background scattering signals generated from parts other than the tip part of a nano-probe.

In addition, a second object of the present invention is to provide a tuning-fork based near-field probe for enabling a spectral measurement by delaying multiple reflections generated by the structure of a nano-probe and by measuring a time-domain transient reaction of a scattering signal.

In addition, a third object of the present invention is to provide a tuning-fork based near-field probe for enabling a precise measurement by stabilizing the mechanical vibration of the near-field probe.

Technical Solution

In order to achieve the above objects, according to one aspect of the present invention, there is provided a tuning-fork based near-field probe for spectral measurement, including: a first electrode and a second electrode arranged apart from each other; and a wire-shaped nano-probe downward attached to a one-side end of the second electrode and configured to vibrate in a perpendicular direction with respect to a sample, wherein the nano-probe includes: a shaft for receiving a terahertz pulse incidented through a means for focusing light; an end part for localizing the receive terahertz pulse to interact with the sample, and scattering a terahertz pulse, into air, which has obtained local information of the sample in the localizing procedure; and a tapered region for connecting the shaft and the end part, wherein the length of the nano-probe, which is defined as a sum of the length of the shaft and the length of the tapered region is formed to be longer than the radius of a focus of a beam by the terahertz pulse which is focused by the means for focusing light.

In addition, according to another aspect of the present invention, there is provided a near-field microscope using a tuning-fork based near-field probe for spectral measurement, the near-field probe microscope including: an optical system configured to include a plurality of beam splitters, a mirror, and a lens for transferring a laser pulse generated by a fast-pulse laser to a terahertz pulse generation device, and to include one or more beam splitters and a plurality of mirrors for transferring a part of the laser pulse generated by the fast-pulse laser to an electric field detector; a sample stand configured to enable a location and a height thereof to be controlled; a plurality of first optical components for transferring and focusing a terahertz pulse generated by the terahertz pulse generation device on a sample; a tuning-fork based near-field probe including a first electrode and a second electrode arranged apart from each other, and a wire-shaped nano-probe downward attached to a one-side end of the second electrode and configured to vibrate in a perpendicular direction with respect to the sample, wherein the nano-probe includes a shaft for receiving a terahertz pulse focused through the first optical components, an end part for allowing the focused terahertz pulse to interact with the sample and scattering a terahertz pulse, into air, which has been subjected to an interaction procedure, and a tapered region for connecting the shaft and the end part; an AC voltage generation device connected to the first and second electrodes of the near-field probe in order to vibrate the near-field probe; an electric field detector for measuring an alternating current flowing through the tuning-fork based near-field probe; a control device for controlling a height of the sample stand to uniformly maintain a distance between the end part of the near-field probe and the sample; a plurality of second optical components for focusing a terahertz pulse directly reflected from the sample and a part of a pulse scattered from the end part of the near-field probe onto the surface of the electric field detector; a lock-in amplifier for demodulating a signal detected through the electric field detector with a vibration frequency of the nano-probe or harmonic of the nano-probe, thereby extracting a component modulated by vibration of the nano-probe; a mechanical optical delay unit for measuring a transient reaction of the terahertz pulse in a time domain; and a control personal computer (control PC) for analyzing the measured transient reaction in a frequency domain, and measuring a characteristic spectrum of the sample, In addition, according to another aspect of the present invention, there is provided a spectral analysis method using a near-field microscope, the method including the steps of: transferring an ultrafast laser pulse generated by a fast-pulse laser to a terahertz generation unit using a plurality of beam splitters, a mechanical chopper, a mechanical optical delay unit, and a mirror; transferring and focusing a terahertz pulse generated by the terahertz generation device onto a sample attached on a piezo-stage; mounting a tuning-fork based near-field probe above the sample and driving the near-field probe, the near-field probe including: a wire-shaped nano-probe downward attached to a one-side end of a second electrode of first and second electrodes arranged apart from each other, and configured to vibrate in a perpendicular direction with respect to the sample; and a wire-shaped knife edge attached to a one-side end of the first electrode to stabilize vibration of the nano-probe; measuring, through an electric field detector, an electric field of a pulse wave scattered from an end part of the near-field probe and a terahertz pulse directly reflected from the sample; demodulating a signal, which is detected through the electric field detector, with a vibration frequency of the nano-probe or a harmonic of the nano-probe through a lock-in amplifier, thereby extracting only a scattered wave of the nano-probe; and recoding a harmonic component detected through the lock-in amplifier while scanning a mechanical delay line, acquiring a time-domain signal, Fourier-transforming the acquired time-domain signal, and performing an analysis in a frequency domain, wherein characteristics of the sample are measured by removing second and third pulse waves by multiple reflections, performing a Fourier transform, and performing an analysis in a frequency domain.

Advantageous Effects

According to the embodiment of the present invention, a near-field microscope includes a tuning fork having a wire-shaped nano-probe which is manufactured with a wire-shaped metal material, vibrates in a perpendicular direction with respect to a sample, and has an appropriate length, thereby minimizing the generation of scattered waves, and thus obtaining a precise scattered wave spectrum.

In addition, since the nano-probe is designed to be sufficiently long, the second or more multiple reflection signals in a time domain is sufficiently delayed in a time domain, so that it is possible to separate the second and third waves from the transient reaction of the first wave.

In addition, when the nano-probe is lengthened, the vibration characteristic may be unstable.

However, since a knife edge having a weight similar to that of a nano-probe is attached to an opposite side of an electrode on which the nano-probe is attached, a mechanical vibration can be stabilized.

BRIEF DESCRIPTION OF THE DRAWINGS

The above objects, and other features and advantages of the present invention will become more apparent after a reading of the following detailed description taken in conjunction with the drawings, in which:

FIG. 3 is a graph and a view explaining the non-linear characteristic of a scattered wave;

FIG. 13 is a view explaining the principle of minimizing the generation of a scattered wave according to an embodiment of the present invention;

FIGS. 14a and 14b are views showing the results of tests for showing a case second and third waves are temporally delayed as the length of a wire-shaped nano-probe is changed;

BEST MODE FOR THE INVENTION

Figure 1:
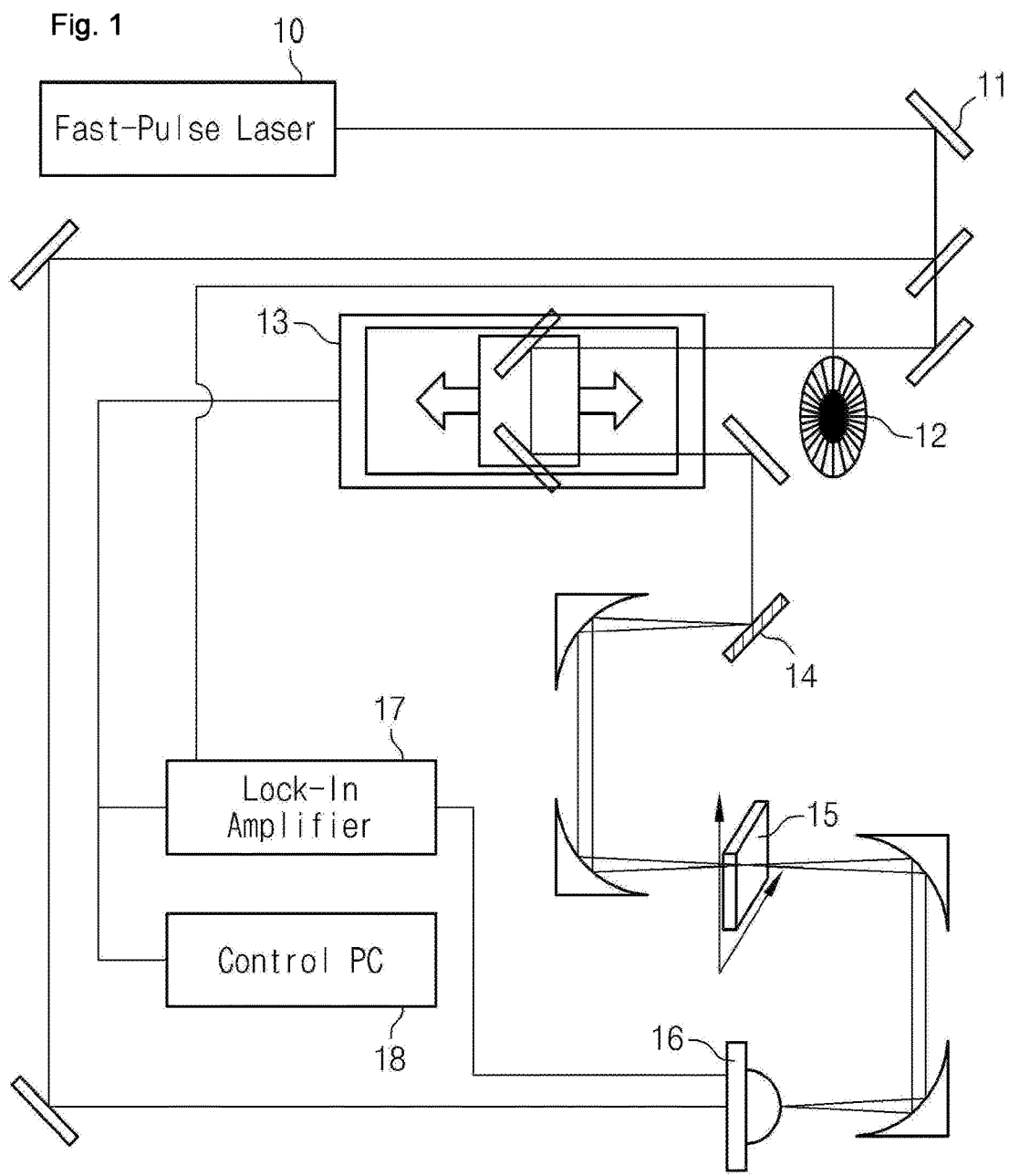
FIG. 1 is a block diagram illustrating the configuration of a conventional near-field microscope to which a terahertz time-domain spectroscopy is applied.
Figure 2:
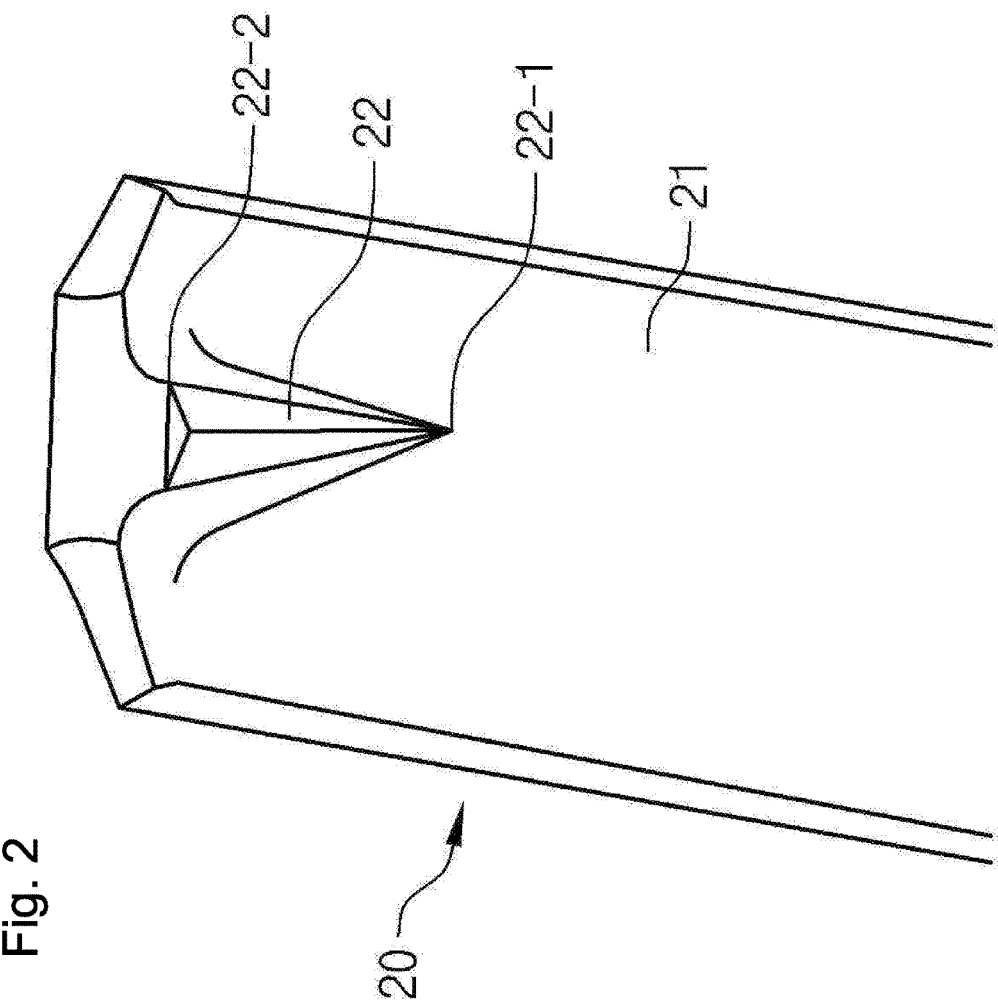
FIG. 2 is a view schematically illustrating a conventional nano-probe.
Figure 4:
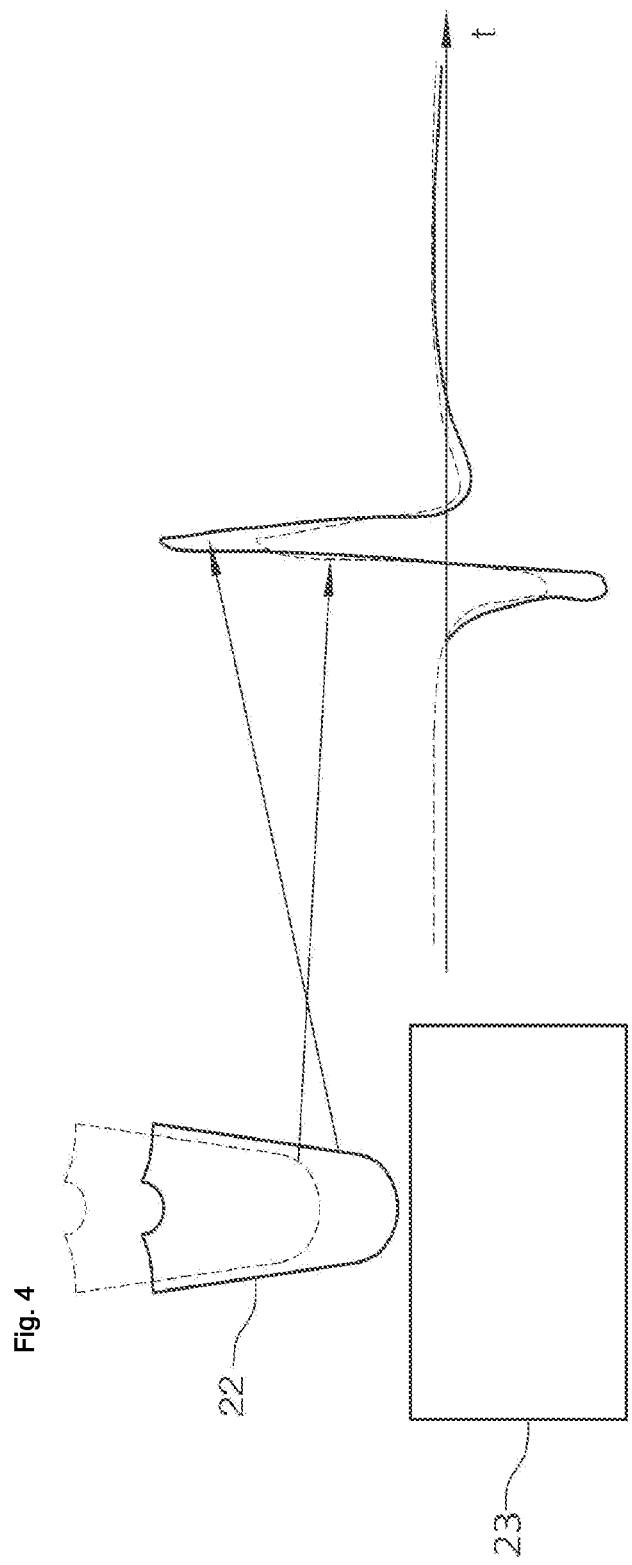
FIG. 4 is a view explaining a method for extracting a scattered wave.
Figure 5:
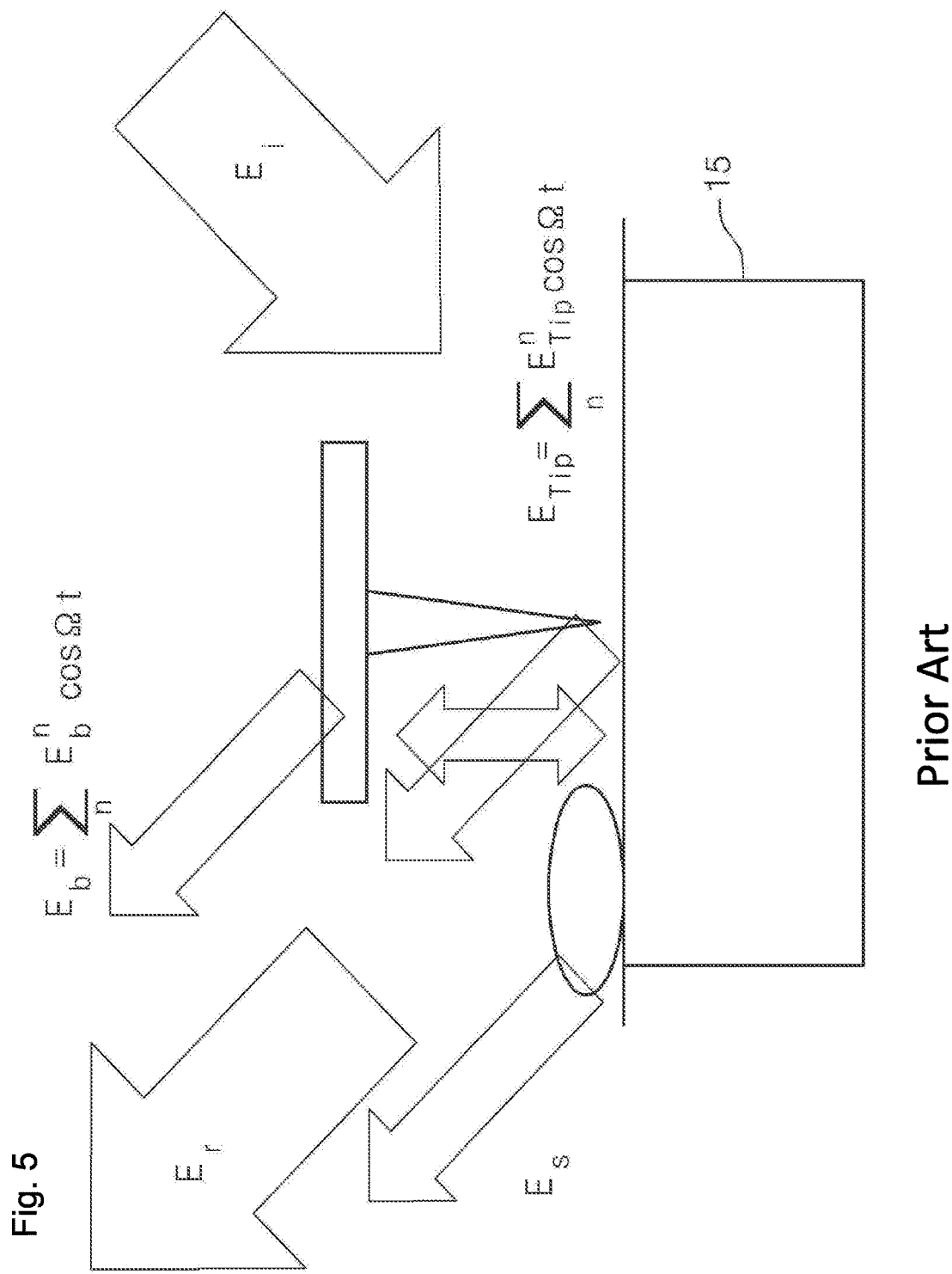
FIG. 5 is a view illustrating various scattering sources which exist in a conventional THz s-SNOM system.
Figure 6:
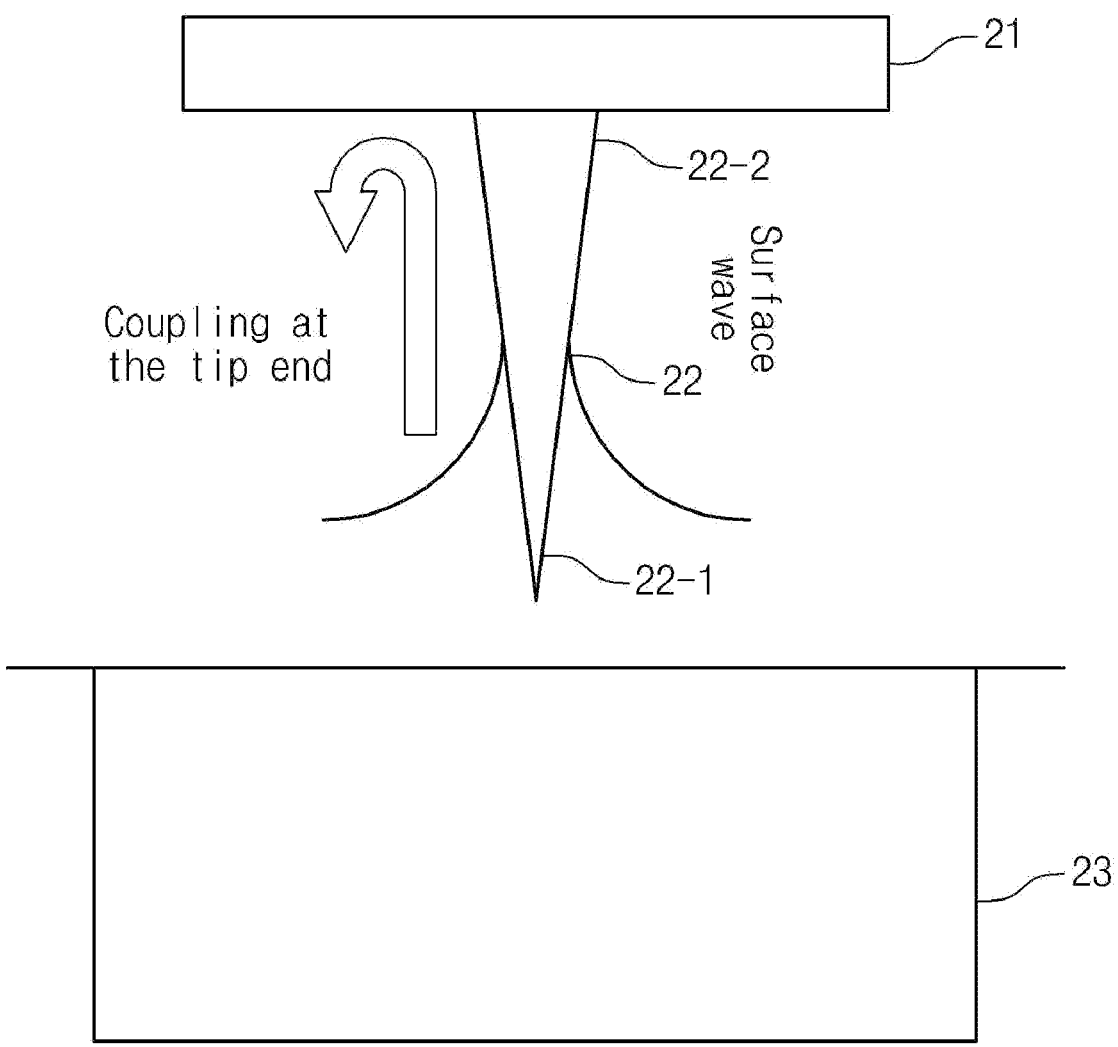
FIG. 6 is a view explaining a Fabry-Ferot interference principle by the wave guide effect of a conventional cantilever-type nano-probe.
Figure 7:
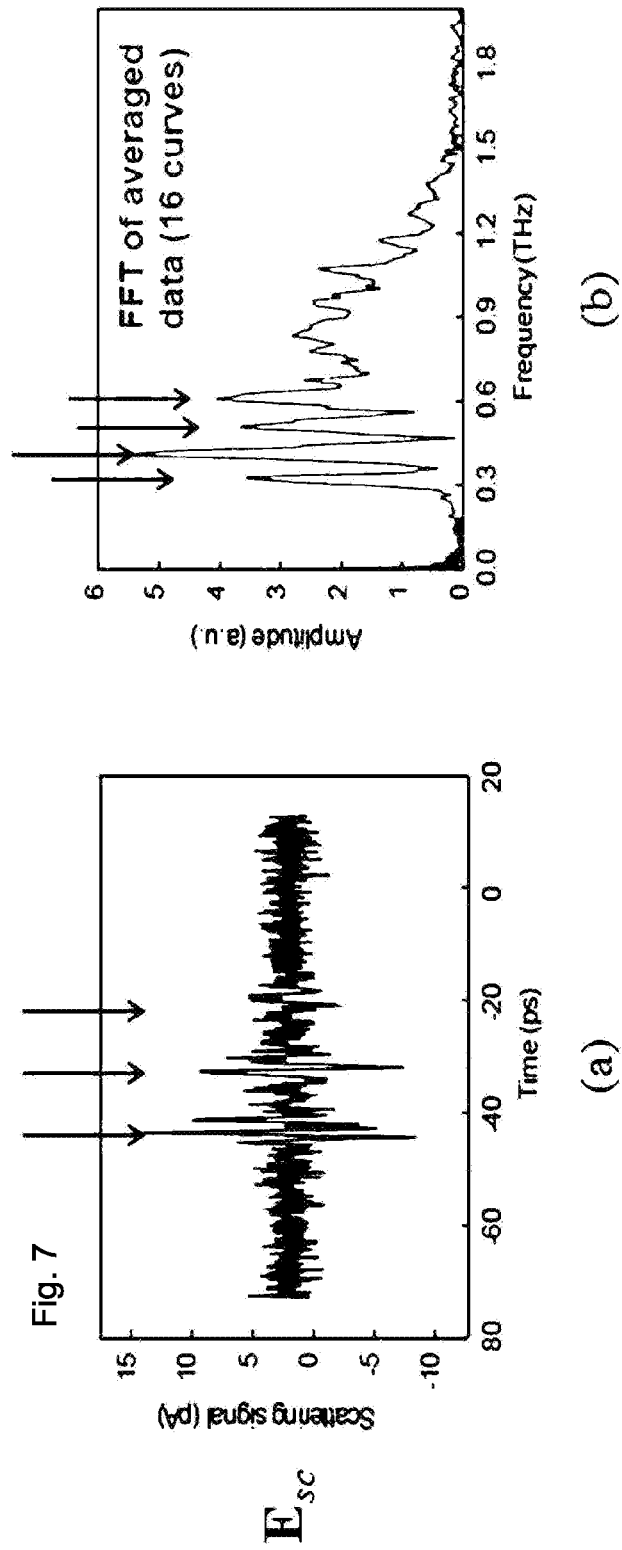
FIG. 7(a) is a waveform view of a time-domain scattering signal generated by multiple reflections.
FIG. 7(b) is a waveform view illustrating multiple peaks which are generated by multiple reflections in a frequency domain.
Figure 8:
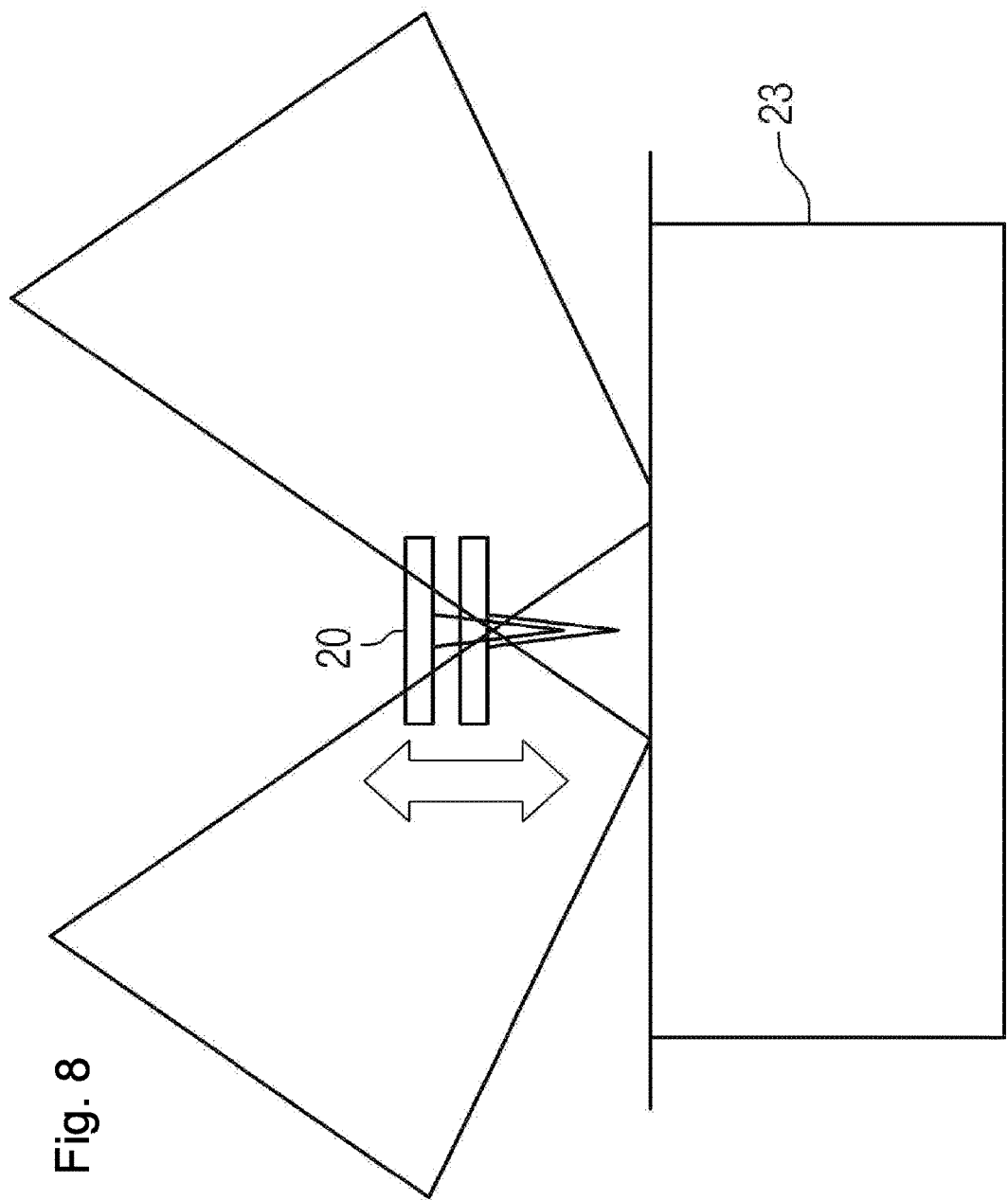
FIG. 8 is a view illustrating a scattered-wave generation region in a conventional cantilever-type nano-probe.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 9:
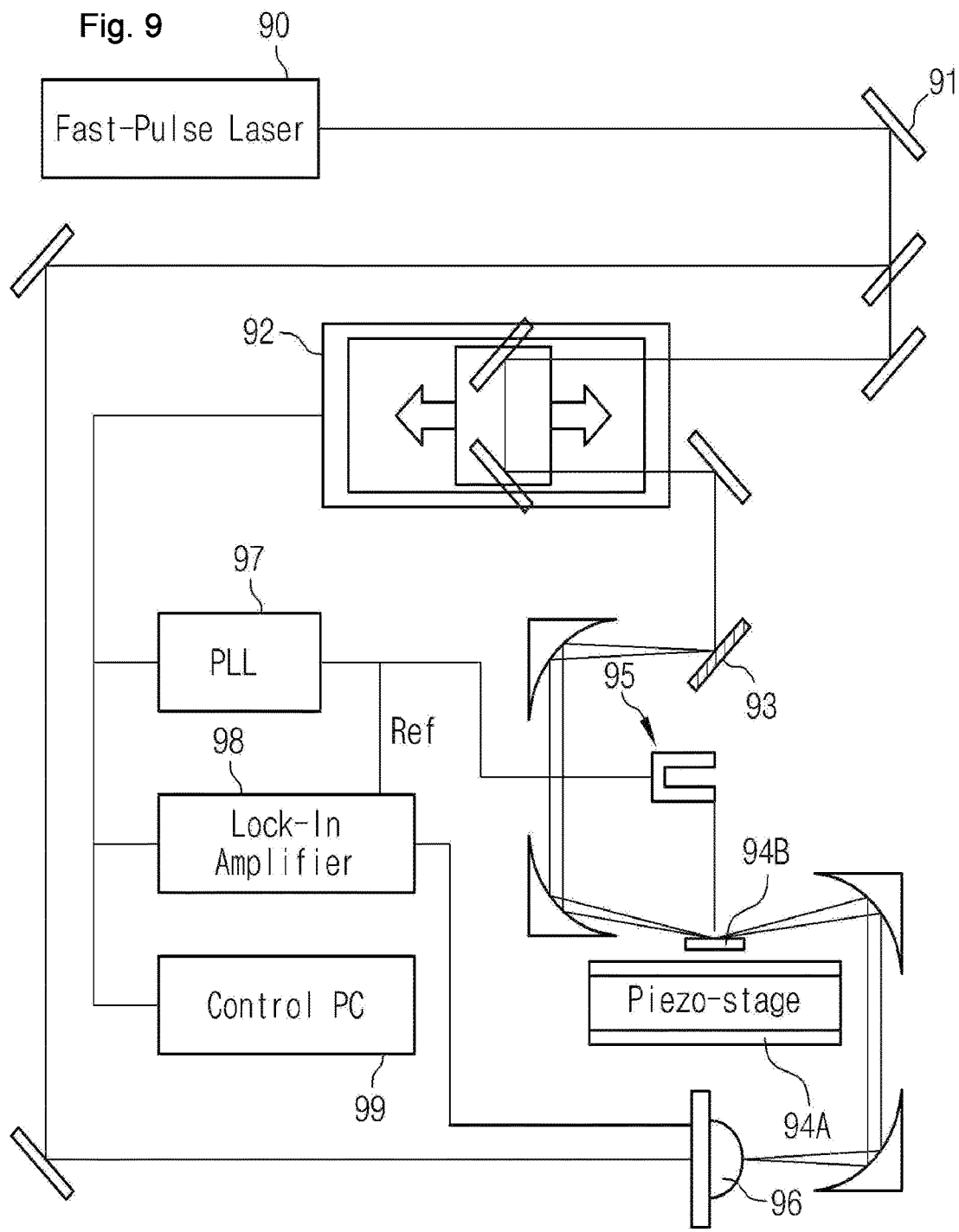
FIG. 9 is a block diagram illustrating the configuration of a resolution improvement device of a near-field microscope according to an embodiment of the present invention.

FIG. 9 is a block diagram illustrating the configuration of a resolution improvement device of a near-field microscope according to an embodiment of the present invention. As illustrated in FIG. 9, a resolution improvement device of a near-field microscope includes a fast-pulse laser 90, a plurality of beam splitters 91, a mechanical optical delay line 92, an InAs wafer 93, a piezo-stage 94A, a sample 94B, a tuning-fork based near-field probe (hereinafter, referred to as a "near-field probe") 95, an electric field detector 96, a phase-locked loop (PLL) 97, a lock-in amplifier 98, and a control personal computer (control PC) 99. A photoconductive antenna (PC antenna) or an electro-optical crystal (EO crystal) may be used as the electric field detector 96. Instead of the InAs wafer 93, an electro-optical crystal (EO crystal), a photoconductive antenna, or the like may be used as a terahertz generation source. Here, the plurality of beam splitters 91, a mechanical chopper (not shown in the drawing), the mechanical optical delay line 92, and the InAs wafer 93 are optical components for generating a terahertz pulse.

FIG. 9 is a block diagram illustrating the configuration of an apertureless type near-field microscope (including an AFM system and a THz-TDS system) wherein a terahertz time-domain spectroscopy is applied to an atomic force microscope (AFM). That is to say, FIG. 9 is a block diagram illustrating the configuration of a near-field microscope using a tuning-fork based near-field probe for a spectral measurement according to an embodiment of the present invention. Here, the near-field microscope includes a tuning fork which has a nano-probe designed to be long so that an artifact by interference between a scattered wave and a reflected wave cannot be produced.

Referring to FIG. 9, the fast-pulse laser 90 generates a visible laser pulse with duration of 100 fs or less. The laser pulse is inputted to the InAs wafer (THz emitter) 93 through the plurality of beam splitters 91 and the mechanical optical delay line 92. Accordingly, a terahertz pulse having a bandwidth of about 0-2.5 THz with duration of 0-1 ps is generated from the InAs wafer 93.

The terahertz pulse generated as above is transferred to the sample 94B attached on the piezo-stage 94A through a first optical component, such as a parabolic mirror or the like. The sample 94B is put on a sample stand (not shown in the drawing) the location and height of which can be controlled. The near-field probe 95 is located above the sample 94B. The material of the near-field probe is quartz, and the near-field probe 95 is connected to the outside through a terminal (not shown in the drawing) thereof. The near-field probe 95 vibrates with a unique frequency (e.g. 25-32 kHz), and has a nano-probe made of a tungsten wire according to an embodiment of the present invention. The nano-probe of the near-field probe 95 is used as a probe of an AFM while being used as a nano-probe of a near-field microscope. Such a near-field probe 95 has an electrical capacitance characteristic, and has a characteristic that the electrical characteristic varies when little force is applied to the nano-probe. Accordingly, the near-field probe 95 is utilized as a force sensor for detecting force applied to the tip part thereof on the basis of the capacitance characteristic thereof.

Figure 10:
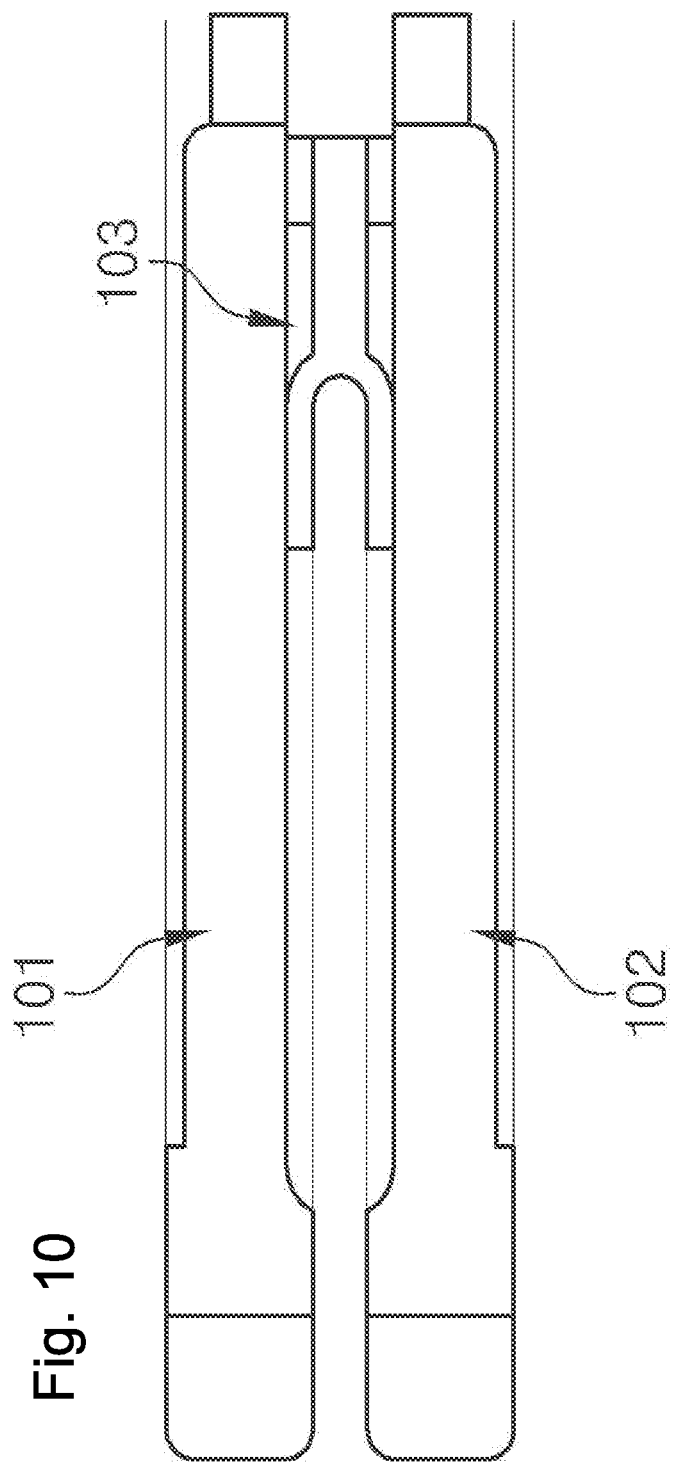
FIG. 10 is a top view of a tuning-fork based near-field probe.
Figure 11:
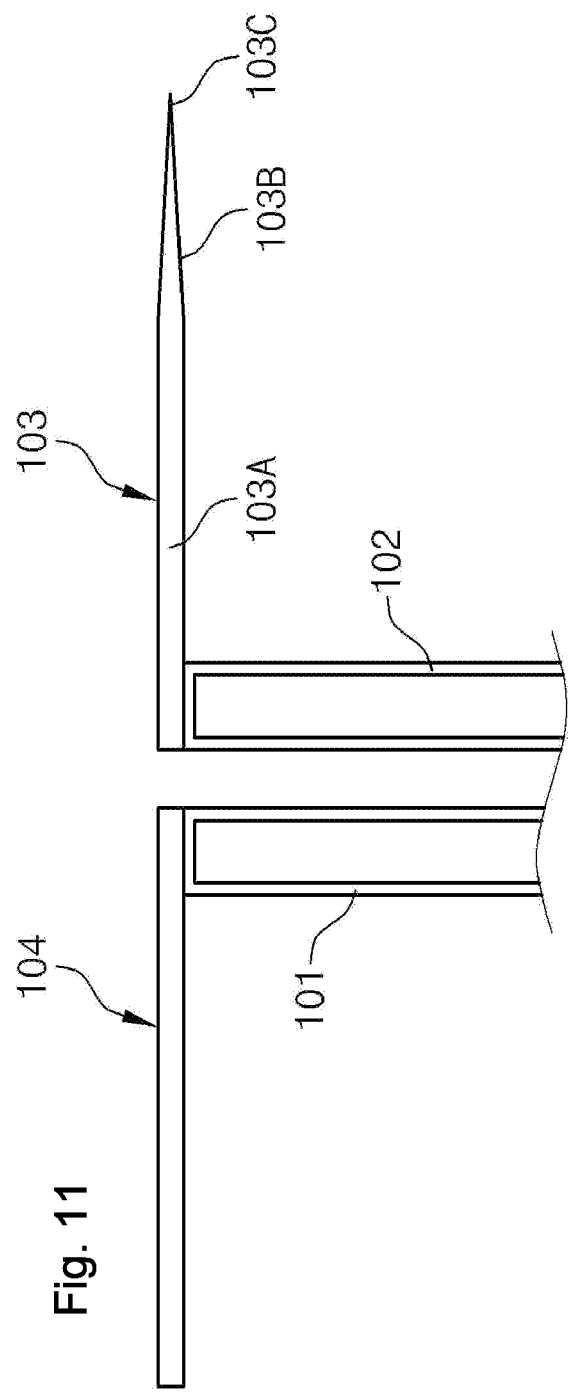
FIG. 11 is a partially detailed view of FIG. 10.

FIG. 10 is a top view illustrating the structure of the near-field probe 95, and FIG. 11 is a partially detailed view of FIG. 10. As illustrated in FIGS. 10 and 11, a second electrode 102 is disposed at a predetermined interval above a first electrode 101, a wire-shaped nano-probe (probe tip) 103 made of a metal material is downward attached to a one-side end of the second electrode 102, and a wire-shaped knife edge 104 is attached to a one-side end of the first electrode 101.

The lower end of the nano-probe 103 is processed to be sharp by an electrochemical etching method, wherein the nano-probe 103 may be variously manufactured to have an available curvature radius in a range of several nm to several tens μm. The knife edge 104 is manufactured to have a length and a weight which are similar to the length and weight of the nano-probe 103, and the end part of the knife edge 104 is manufactured in the shape of a blade. The knife edge 104 is located at a surface corresponding to the nano-probe 103, and functions to stabilize the vibration of the nano-probe 103.

The nano-probe 103 is constituted by a tip shaft 103A, a tapered region 103B, and a tip end 103C. The tip shaft 103A functions to receive a terahertz pulse incidented through a parabolic mirror or the like. The tapered region 103B functions to receive a terahertz pulse applied from the tip shaft 103A, and to focus the received terahertz pulse onto the tip end 103C. As the available radius of the tip end 103C decreases, the amount of terahertz pulse focused onto the tip end 103C increases. As the amount of terahertz pulse focused onto the tip end 103C increases, a higher resolution can be achieved. The tip end 103C functions to scatter a terahertz pulse including information on the sample 94B into the air in interaction with the sample 94B by the focused terahertz pulse.

Although the diameter of the nano-probe 103 is not specifically limited, it has been identified as a test result that a desirable test result is outputted when the diameter of the tip shaft 103A is 1 μm or more, and the available radius of the tip end 103C is 1 nm or more. Although the material of the nano-probe 103 also is not specifically limited, it has been found as a test result that compound materials including: a dielectric including a semiconductor or a metallic material, such as tungsten, platinum, gold, or the like; and a dielectric on which a metal is coated produce desirable test results. In addition, conductive materials, such as a carbon fiber, a carbon nano-tube, or the like, may be used as well.

As a test result, it has been found that, when the length of the nano-probe 103 is equal to or longer than a half of the diameter of the focus of a terahertz pulse focused onto the nano-probe, a desirable test result is outputted. In addition, it has been found that, in the case where a broadband pulse light source generating an incident wave with a bandwidth in a range of $f_1$-$f_2$ ($f_1$<$f_2$) is employed, a desirable test result is outputted when the length of the nano-probe 103 is equal to or longer than $c/2f_1$ (wherein "c" represents the speed of light in vacuum). In addition, it has been found that, in the case where a time window required for measuring a scattered wave in order to remove a Fabry-Ferot phenomenon in a time domain is set to "T", a desirable test result is outputted when the length "L" of the nano-probe 103 meets a condition of "2L>cT". In addition, it has been found that, in the case where a broadband pulse light source generating an incident wave with a bandwidth in a range of $f_1$-$f_2$ ($f_1$<$f_2$) is employed, a desirable test result is outputted when the length of the nano-probe 103 is set to meet a condition of "$c/f_1$=$L_1$".

When a sine wave signal corresponding to a resonance frequency (e.g. 25-32 kHz) supplied from an AC voltage source (not shown in the drawing) is applied to the first electrode 101 and the second electrode 102, the first electrode 101 and the second electrode 102 vibrate thereby. In this case, as described above, the knife edge 104 is attached to the one-side end of the first electrode 101, and the nano-probe 103 is attached to the one-side end of the second electrode 102. Accordingly, the nano-probe 103 and the knife edge 104 vibrate in a perpendicular direction with respect to the sample 94B.

That is to say, the near-field probe 95 functions to measure an atomic force operating between the surface of the sample 94B and the tip end 103C of the nano-probe 103 while mechanically vibrating as described above. That is to say, the near-field probe 95 is an element having two terminals like a resistor, wherein a relation between the voltage and the current of the element varies depending on force operating between the nano-probe 103 and the sample 94B, and on the basis of the variation, the force is measured and a distance is controlled. The effective value of current flowing between the first electrode 101 and second electrode 102 is connected with force operating between the tip end 103C of the nano-probe 103 and the sample 94B. Therefore, a control device (not shown in the drawing) can monitor the effective value of the current, and can uniformly maintain an average distance between the sample 94B and the nano-probe 103 on the basis of a result of the monitoring. Here, the average distance between the sample 94B and the nano-probe 103 is obtained by measuring the characteristics of the near-field probe 95, and the average distance is uniformly maintained by performing a PID control on the piezo-stage 94A.

Figure 12:
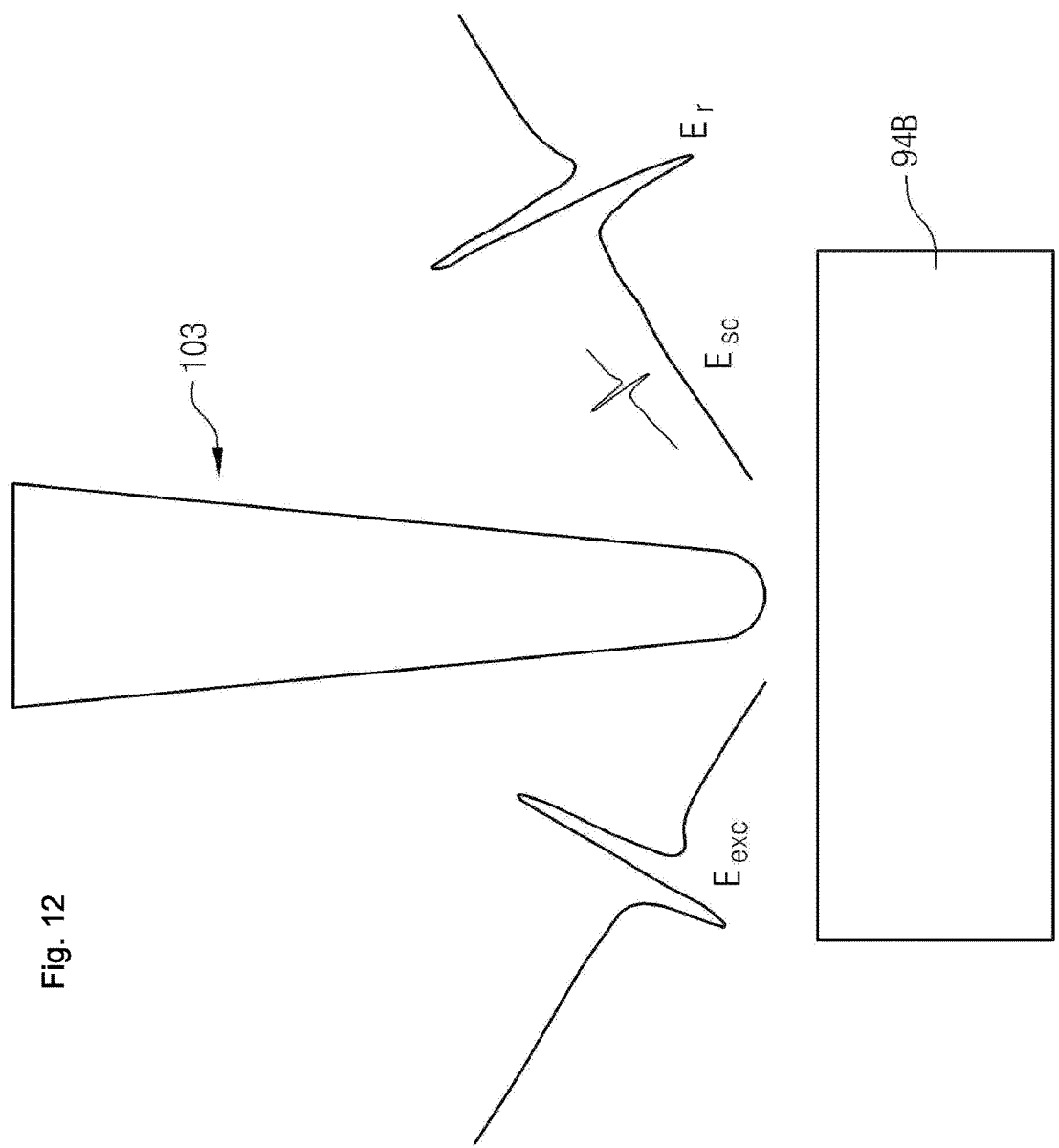
FIG. 12 is a view illustrating a nano-probe and a scattered wave at the tip part of the probe.

In such a state, a three-dimensional topography of the sample 94B can be obtained by scanning the sample 94B, which will be described in more detail with reference to FIG. 12.

Through the route as described above, a terahertz pulse is focused on the nano-probe 103 in driving as described above. In FIG. 12, an incident wave of the nano-probe 103 is denoted as "$E_{exc}$", a reflected wave is denoted as "$E_r$", and a scattered wave generated from the tip end of the nano-probe 103 is denoted as "$E_{sc}$". The characteristics of the scattered wave "$E_{sc}$" is determined by the material of the tip end of the nano-probe 103 and by a local optical constant of the sample 94B which is located just below of the nano-probe 103. Therefore, when the scattered wave "$E_{sc}$" is accurately measured, and an appropriate theoretical technique is applied to a result of the measurement, the optical characteristic of the sample 94B located just below the nano-probe 103 can be extracted. A degree of the localization is proportional to the diameter (size) of the tip end 103C of the nano-probe 103. Therefore, as a nano-probe 103 with a tip end 103C having a shorter diameter is used, a more improved resolution is obtained. For example, when a nano-probe 103 with a tip end 103C having a diameter in a nanometer size is used, a nanometer-level resolution can be obtained.

Since the near-field probe 95 attached to the base part of the nano-probe 103 vibrates with a unique frequency "Ω" in a perpendicular direction with respect to the sample 94B, as described above, a scattered wave generated from the tip end 103C of the nano-probe 103 may be expressed as a sum of the "Ω" and harmonic components, as Equation 2 below.

$$E_{sc}(t) = \sum_{m=1}^{\infty} E_m \cos(m\Omega t) \qquad (2)$$

Therefore, by extracting the harmonic components and omega "Ω" on the sample 94B through the electric field detector 96 and the lock-in amplifier 98, it is possible to measure only a scattered wave without interference with a reflected wave and a scattered wave at each position when measuring the scattered wave at the tip end 103C of the nano-probe 103.

As described above, the nano-probe 103 according to an embodiment of the present invention is made of a wire-shaped metal material having a constant thickness and is configured to have a structure of vibrating in a length direction with respect to the sample 94B. In addition, the shaft of the nano-probe 103 is manufactured to be longer than the radius of a terahertz beam at a focus. Therefore, the generation of a scattered wave at the base part of the nano-probe 103 is minimized. FIG. 13 is a view illustrating the principle that the generation of a scattered wave is minimized, as described above, when a nano-probe 103 according to an embodiment of the present invention is used.

Delaying a multiple reflection phenomenon of a scattered wave according to an embodiment of the present invention will now be described with reference to FIGS. 14a and 14b.

A pulse wave incidented to the tip end 103C of the nano-probe 103 excites the surface wave of the shaft part. The surface wave excited as described above is propagated to and reflected from the base part of the nano-probe 103 (see FIGS. 15, 14a and 14b). When the nano-probe 103 has a length of "L", a second scattered pulse is generated after a time of "2L/c" (wherein, "c" represents the velocity of light) has elapsed. The scattered pulse generated as above makes it difficult to achieve a spectral analysis on a measured time-domain scattering signal. However, as described above, since the length of the nano-probe 103 is long (e.g. 4 mm or longer), the generation of second and higher multiple reflected signals in a time domain is temporally delayed. Therefore, by making a second pulse arrive after the transient signal of a scattering signal by a first pulse is terminated, it is possible to separate two signals in a time domain. Accordingly, it is possible to separate only a time-domain signal by a first pulse and to analyze the spectrum thereof, and thus a precise scattered wave spectrum can be obtained.

FIGS. 14a and 14b shows the results of tests for verifying that second and third pulses of a time-domain scattering signal generated by a multiple reflection phenomenon are temporally delayed as the length of the nano-probe 103 is lengthened according to an embodiment of the present invention.

Figure 15:
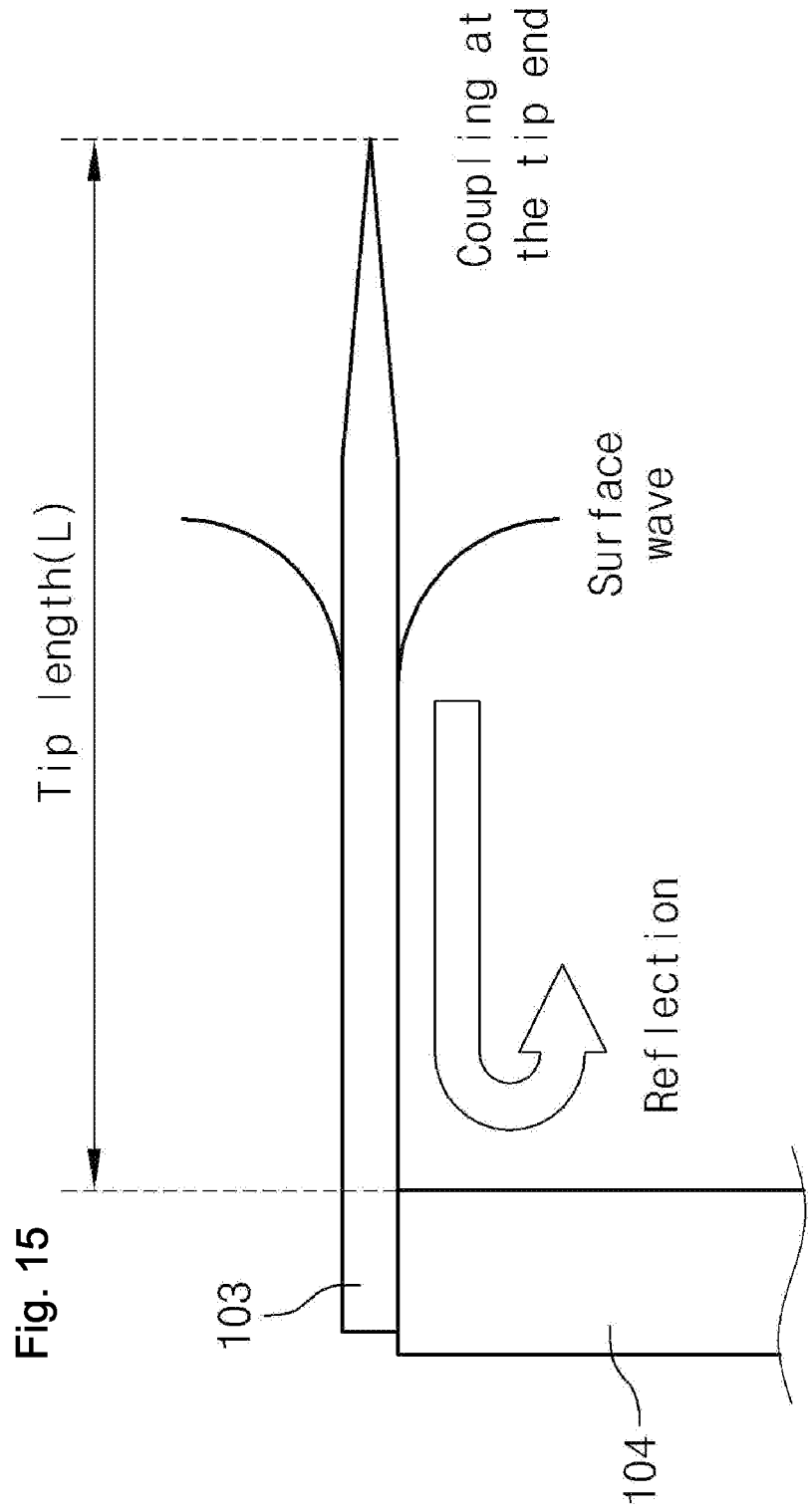
FIG. 15 is a view showing a reason of generation of second and third scattered waves in a wire-shaped nano-probe.

FIG. 15 is a view showing a reason of multiple reflections generated on a wire-shaped nano-probe 103.

The electric field detector 96 is a terahertz detection device, and is configured to directly measure an electric field in a terahertz wave domain on the sample 94B and to output a measured signal to the lock-in amplifier 98.

The lock-in amplifier 98 extracts the omega "Ω" or harmonic components thereof on the basis of the measured signal of the electric field inputted from the electric field detector 96.

The control personal computer (control PC) 99 records the harmonic components extracted through the lock-in amplifier 98 while scanning the mechanical optical delay line 92, which is a mechanical delay line, thereby obtaining a time-domain signal, performing a Fourier transform on the obtained time-domain signal, and performing an analysis in a frequency domain. Accordingly, the broadband sample characteristic of the sample 94B can be measured.

Figure 16:
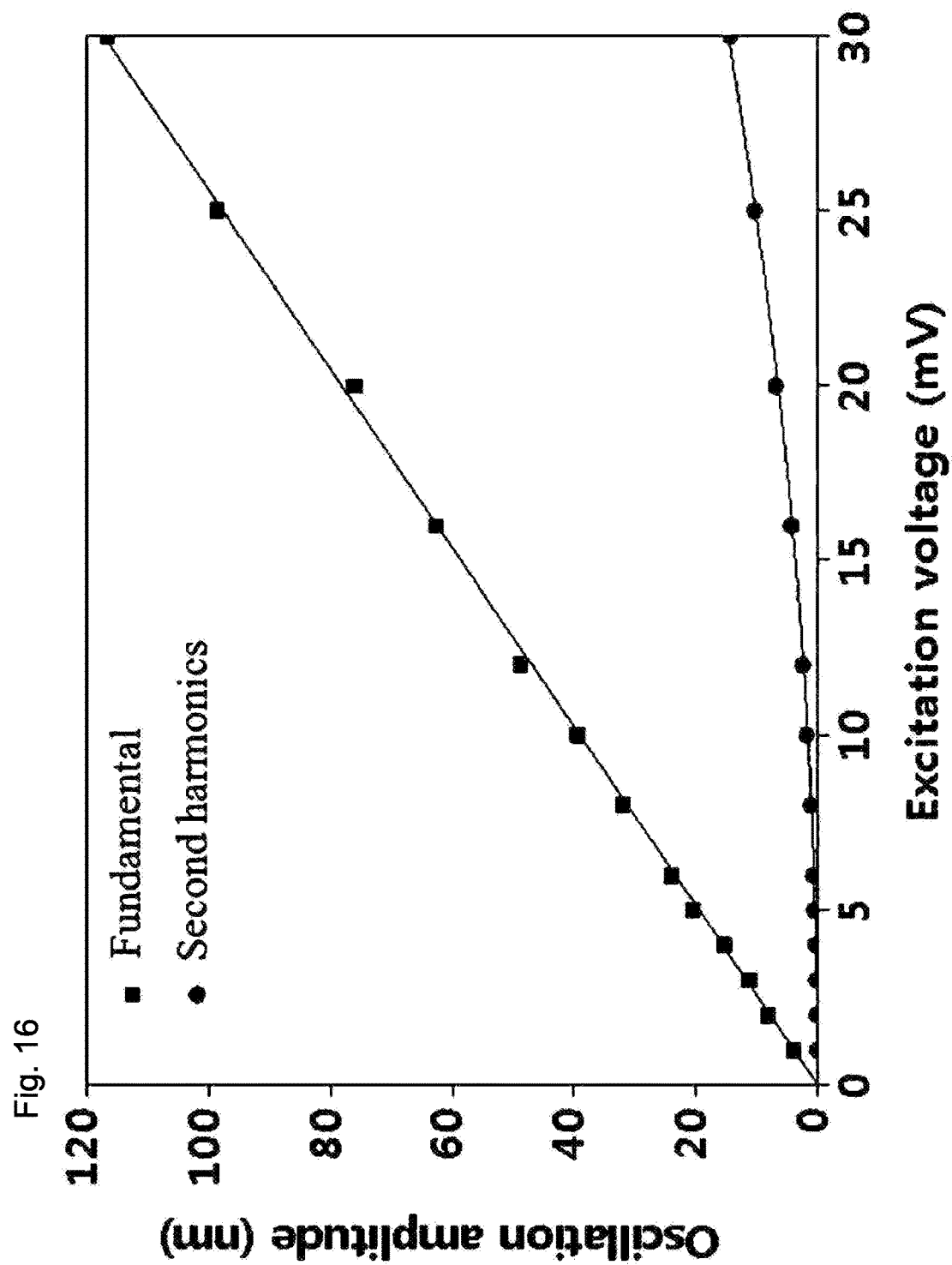
FIG. 16 is a graph illustrating a relation between an amplitude and a voltage applied to a tuning-fork based near-field probe.

FIG. 16 is a graph illustrating a relation between an amplitude and a voltage applied to the near-field probe 95. Here, the horizontal axis represents the magnitude (peak to peak) of a voltage applied to the near-field probe 95, and the vertical axis represents an amplitude. Although an ideal sine wave is applied to the near-field probe 95, it is impossible to have the form of a complete sine wave due to mechanical vibration thereby. Generally, there are mechanical vibration components corresponding to two or three times a sine wave frequency applied to the near-field probe 95. In the graph of FIG. 16, "Fundamental" and "Second Harmonics" represent the omega component of the mechanical vibration of the near-field probe 95 and a double of the omega component, respectively. The near-field probe 95 is generally driven with an amplitude of about 100 nm, and may be driven with an amplitude in a range of several nm to several hundred nm.

It is very important to make vibration in the form of a stable sine wave on the principle of measurement. To this end, a wire-shaped knife edge 104 for stabilizing vibration is mounted on the electrode 101 which is opposite to the electrode 102 on which the wire-shaped nano-probe 103 is mounted, which makes it possible to obtain mechanical vibration similar to a sine wave.

Although a preferred embodiment of the present invention has been described for illustrative purposes, those skilled in the art will appreciate that various modifications, additions and substitutions are possible, without departing from the scope and the spirit of the invention as disclosed in the accompanying claims.

The invention claimed is:

1. A tuning-fork based near-field probe for spectral measurement, comprising:
   a first electrode and a second electrode arranged apart from each other; and
   a wire-shaped nano-probe downward attached to a one-side end of the second electrode and configured to vibrate in a perpendicular direction with respect to a sample,
   wherein the nano-probe comprises:
   a shaft for receiving a terahertz pulse incident through a means for focusing light;
   an end part for localizing the received terahertz pulse to interact with the sample, and scattering a terahertz pulse, into air, which has obtained local information of the sample in a localizing procedure; and
   a tapered region for connecting the shaft and the end part, wherein a length of the nano-probe, which is defined as a sum of a length of the shaft and a length of the tapered region is formed to be longer than a radius of a focus of a beam by the terahertz pulse which is focused by the means for focusing light.

2. The tuning-fork based near-field probe according to claim 1, wherein a material of the nano-probe is tungsten or a conductive metal.

3. The tuning-fork based near-field probe according to claim 1, wherein, in order to stabilize vibration of the nano-probe, the first electrode is provided on a one-side end thereof with a knife edge having a length and a weight which are equal to those of the nano-probe.

4. The tuning-fork based near-field probe according to claim 3, wherein the knife edge is made of a material equal to that of the nano-probe, and has a shape of a blade at an end part thereof.

5. The tuning-fork based near-field probe according to claim 1, wherein the shaft has a diameter of 1 μm or more, and the end part has an available radius of 10 nm or more.

6. The tuning-fork based near-field probe according to claim 1, wherein the length of the nano-probe is equal to or greater than 3 mm.

7. The tuning-fork based near-field probe according to claim 1, wherein the length of the nano-probe is equal to or greater than $c/2f_1$ where the terahertz pulse is a broadband pulse light source having a frequency band in a range of $f_1$-$f_2$ (where "c" is the velocity of light, $f_1$ is a first frequency of the terahertz pulse, $f_2$ is a second frequency of the terahertz pulse, and $f_1 < f_2$).

8. The tuning-fork based near-field probe according to claim 1, wherein the length of the nano-probe is equal to or greater than "cT/2" (where "c" is the velocity of light and "T" is a duration of a transient reaction of the scattered terahertz pulse generated by interaction between the end part and the sample).

9. A near-field microscope using a tuning-fork based near-field probe for spectral measurement, the near-field probe microscope comprising:
   an optical system configured to include a plurality of beam splitters, a mirror, and a lens for transferring a laser pulse generated by a fast-pulse laser to a terahertz pulse generation device, and to include one or more beam splitters and a plurality of mirrors for transferring a part of the laser pulse generated by the fast-pulse laser to an electric field detector;

a sample stand configured to enable a location and a height thereof to be controlled;

a plurality of first optical components for transferring and focusing a terahertz pulse generated by the terahertz pulse generation device on a sample;

a tuning-fork based near-field probe comprising a first electrode and a second electrode arranged apart from each other, and a wire-shaped nano-probe downward attached to a one-side end of the second electrode and configured to vibrate in a perpendicular direction with respect to the sample, wherein the nano-probe includes a shaft for receiving a terahertz pulse focused through the first optical components, an end part for allowing the focused terahertz pulse to interact with the sample and scattering a terahertz pulse, into air, which has been subjected to an interaction procedure, and a tapered region for connecting the shaft and the end part;

an AC voltage generation device connected to the first and second electrodes of the near-field probe in order to vibrate the near-field probe;

an electric field detector for measuring an alternating current flowing through the tuning-fork based near-field probe;

a control device for controlling a height of the sample stand to uniformly maintain a distance between the end part of the near-field probe and the sample;

a plurality of second optical components for focusing a terahertz pulse directly reflected from the sample and a part of a pulse scattered from the end part of the near-field probe onto the surface of the electric field detector;

a lock-in amplifier for demodulating a signal detected through the electric field detector with a vibration frequency of the nano-probe or harmonic of the nano-probe, thereby extracting a component modulated by vibration of the nano-probe;

a mechanical optical delay unit for measuring a transient reaction of the terahertz pulse in a time domain; and a control personal computer (control PC) for analyzing the measured transient reaction in a frequency domain, and measuring a characteristic spectrum of the sample, wherein a length of the nano-probe, which is a sum of a length of the shaft and a length of the tapered region, is longer than a radius of a focus of a terahertz beam focused by a means for focusing light.

10. The near-field microscope according to claim 9, wherein the near-field probe is driven with 25-32 kHz.

11. The near-field microscope according to claim 9, wherein a material of the nano-probe is tungsten or a conductive metal.

12. The near-field microscope according to claim 9, wherein, in order to stabilize vibration of the nano-probe, the first electrode is provided on a one-side end thereof with a knife edge having a length and a weight which are equal to those of the nano-probe.

13. The near-field microscope according to claim 12, wherein the knife edge is made of a material equal to that of the nano-probe, and has a shape of a blade at an end part thereof.

14. The near-field microscope according to claim 9, wherein the shaft has a diameter of 1 µm or more, and the end part has an available radius of 10 nm or more.

15. The near-field microscope according to claim 9, wherein the length of the nano-probe is equal to or greater than 3 mm.

16. The near-field microscope according to claim 9, wherein the length of the nano-probe is equal to or greater than $c/2f_1$ where the terahertz pulse is a broadband pulse light source having a frequency band in a range of $f_1$-$f_2$ (where "c" is the velocity of light, $f_1$ is a first frequency of the terahertz pulse, $f_2$ is a second frequency of the terahertz pulse, and $f_1<f_2$).

17. The near-field microscope according to claim 9, wherein the length of the nano-probe is equal to or greater than "cT/2" (where "c" is the velocity of light and "T" is a duration of a transient reaction of the scattered terahertz pulse generated by interaction between the end part and the sample).

18. The near-field microscope according to claim 9, wherein the terahertz pulse generation device comprises an electro-optical crystal or a photoconductive antenna including metal electrodes facing each other on a semiconductor crystal or a semiconductor crystal, such as InAs, GaAs, or the like.

19. The near-field microscope according to claim 9, wherein the terahertz detection device comprises a photoconductive antenna or an electro-optical crystal.

20. The near-field microscope according to claim 9, wherein the direction of a magnetic field of a terahertz pulse generated by the terahertz pulse generation device is perpendicular to the probe.

21. A spectral analysis method using a near-field microscope, the method comprising the steps of:

(a) transferring an ultrafast laser pulse generated by a fast-pulse laser to a terahertz generation unit using a plurality of beam splitters, a mechanical chopper, a mechanical optical delay unit, and a mirror;

(b) transferring and focusing a terahertz pulse generated by the terahertz generation device onto a sample attached on a piezo-stage;

(c) mounting a tuning-fork based near-field probe above the sample and driving the near-field probe, the near-field probe comprising: a wire-shaped nano-probe downward attached to a one-side end of a second electrode of first and second electrodes arranged apart from each other, and configured to vibrate in a perpendicular direction with respect to the sample; and a wire-shaped knife edge attached to a one-side end of the first electrode to stabilize vibration of the nano-probe;

(d) measuring, through an electric field detector, an electric field of a pulse wave scattered from an end part of the near-field probe and a terahertz pulse directly reflected from the sample;

(e) demodulating a signal, which is detected through the electric field detector, with a vibration frequency of the nano-probe or a harmonic of the nano-probe through a lock-in amplifier, thereby extracting only a scattered wave of the nano-probe; and (f) recoding a harmonic component detected through the lock-in amplifier while scanning a mechanical delay line, acquiring a time-domain signal, Fourier-transforming the acquired time-domain signal, and performing an analysis in a frequency domain, wherein characteristics of the sample are measured by removing second and third pulse waves by multiple reflections, performing a Fourier transform, and performing an analysis in a frequency domain.

* * * * *